(12) United States Patent
Kourtakis et al.

(10) Patent No.: US 6,696,388 B2
(45) Date of Patent: Feb. 24, 2004

(54) GEL CATALYSTS AND PROCESS FOR PREPARING THEREOF

(75) Inventors: Kostantinos Kourtakis, Swedesboro, NJ (US); Leo E. Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 27 days.

(21) Appl. No.: 09/757,440

(22) Filed: Jan. 10, 2001

(65) Prior Publication Data

US 2003/0023126 A1 Jan. 30, 2003

Related U.S. Application Data

(60) Provisional application No. 60/189,765, filed on Mar. 16, 2000, and provisional application No. 60/177,795, filed on Jan. 24, 2000.

(51) Int. Cl.$^7$ ............... B01J 21/16; B01J 21/18; B01J 23/02; B01J 23/06; B01J 23/40
(52) U.S. Cl. ............ 502/320; 502/74; 502/84; 502/104; 502/110; 502/113; 502/117; 502/183; 502/184; 502/185; 502/208; 502/209; 502/210; 502/211; 502/212; 502/213; 502/219; 502/220; 502/221; 502/222; 502/223; 502/241; 502/242; 502/243; 502/244; 502/245; 502/246; 502/247; 502/248; 502/249; 502/250; 502/251; 502/252; 502/253; 502/254; 502/255; 502/256; 502/257; 502/258; 501/117
(58) Field of Search ................ 502/256, 257, 502/306–320, 323, 439, 405, 714, 84, 104, 110, 113, 117, 208–213, 219–223, 241–262, 302–355

(56) References Cited

U.S. PATENT DOCUMENTS

| | | | | |
|---|---|---|---|---|
| 4,032,434 A | * | 6/1977 | Rausch | 208/139 |
| 4,053,437 A | * | 10/1977 | Liu et al. | 252/458 |
| 4,151,122 A | | 4/1979 | McDaniel et al. | |
| 4,171,259 A | * | 10/1979 | Eberly, Jr. | 208/139 |
| 4,219,447 A | * | 8/1980 | Wheelock | 252/466 PT |
| 4,433,190 A | * | 2/1984 | Sikkenga et al. | 585/660 |
| 4,439,534 A | | 3/1984 | Foulletier | |
| 4,513,162 A | | 4/1985 | Al-Muddarris | |
| 4,591,429 A | * | 5/1986 | Ho et al. | 208/254 |
| 4,946,820 A | | 8/1990 | Lane | |
| 5,198,404 A | * | 3/1993 | Arndt et al. | 502/230 |
| 5,242,883 A | * | 9/1993 | Ichikawa et al. | 502/439 |
| 5,290,748 A | * | 3/1994 | Knuuttila et al. | 502/228 |
| 5,378,350 A | | 1/1995 | Zimmermann | |
| 5,595,953 A | * | 1/1997 | McDaniel et al. | 502/237 |
| 5,834,572 A | * | 11/1998 | Derleth et al. | 526/126 |
| 6,008,154 A | * | 12/1999 | Rosendorfer et al. | 502/319 |
| 6,235,677 B1 | * | 5/2001 | Manzer et al. | 502/232 |
| 6,353,035 B2 | * | 3/2002 | Manzer et al. | 518/700 |
| 6,413,903 B1 | * | 7/2002 | Kourtakis | 502/209 |
| 6,475,950 B2 | * | 11/2002 | Kourtakis et al. | 502/319 |

FOREIGN PATENT DOCUMENTS

EP 947 247 10/1999

OTHER PUBLICATIONS

Weckhuysen, Bert M., Alkane Dehydrogenation Over Supported Chromium Oxide Catalysts, Catalysis Today 51 (1999) pp. 223–232.

Baker, et al. Mixed Gels of Vanadia and Silica: Structural Properties and Catalystic Behavior in Selective Reduction of Nitric Oxide with Ammonia, Journal of Catalysis,(1988) pp. 273–285, vol. 111 (Switzerland).

* cited by examiner

Primary Examiner—Cam N. Nguyen

(57) ABSTRACT

A gel composition substantially contained within the pores of a solid material for use as a catalyst or as a catalyst support in dehydrogenation and dehydrocyclization processes.

8 Claims, No Drawings

GEL CATALYSTS AND PROCESS FOR PREPARING THEREOF

This application claims the benefit of the filing date of U.S. Provisional Application No. 60/177,795, which was filed on Jan. 24, 2000 (now pending); and U.S. Provisional Application No. 60/189,765, which was filed on Mar. 16, 2000, (now pending).

FIELD OF THE INVENTION

The present invention relates to a novel composition comprising a gel that has utility as a catalyst or as a catalyst support. Also disclosed are methods of preparing the compositions and processes for using the compositions for the dehydrogenation of $C_{2-10}$ hydrocarbons.

BACKGROUND OF THE INVENTION

The dehydrogenation of paraffins to olefins is commercially significant because of the need for olefins for the manufacture of high octane gasolines, elastomers, detergents, plastics, ion-exchange resins and pharmaceuticals. Important hydrocarbon dehydrocyclization reactions include the conversion of diisobutylene and isooctane to p-xylene.

Processes for the conversion of paraffin hydrocarbons to less saturated hydrocarbons are known. For examples, see U.S. Pat. No. 4,513,162, U.S. Pat. No. 5,378,350 and European Pat. Application EP 947,247 (published). Nonetheless, there is a continuing need to develop new compositions that are more effective catalysts than those currently available in dehydrogenation processes.

SUMMARY OF THE INVENTION

The present invention discloses a composition of matter, comprising: (i) a solid material having pores; (ii) a gel, said gel being substantially contained within the pores of said solid material and comprising at least one catalytically active element, and optionally when said catalytically active element is other than Cr, comprising chromium in addition to said element.

Another disclosure of the present invention is a process for preparing a composition of matter comprising: a solid material having pores; a gel, said gel being substantially contained within the pores of said solid material and comprising at least one catalytically active element, and optionally when said catalytically active element is other than Cr, comprising Cr in addition to said element, said process comprising: contacting in the presence of a solid material having pores, in any order a protic solution with a non-aqueous solution wherein said non-aqueous solution comprises a gel-forming precursor and wherein one of either the protic solution or the non-aqueous solution comprises at least one soluble compound comprising an inorganic element selected from the group consisting of Group 1 through Group 16 and the lanthanides of the Periodic Table, under conditions such that the solution added first is at incipient wetness, whereby gel formation occurs substantially within the pores of said solid material.

A further disclosure of the present invention is a composition of matter prepared by the process described immediately above.

The present invention also discloses an improved gel composition, wherein said improvement comprises: said gel is substantially contained within the pores of a solid material.

Yet another disclosure of the present invention is a method of using the composition disclosed wherein said method comprises contacting in a reactor said composition with a hydrocarbon feed in a dehydrogenation or dehydrocyclization process, said hydrocarbon being from $C_2$ to $C_{10}$.

DETAILED DESCRIPTION OF THE INVENTION

The solid material having pores is selected from the group consisting of alumina, silica, titania, zirconia, carbon, molecular sieves (for example, zeolites), porous minerals (such as bentonite), microporous, mesoporous and macroporous materials, montmorillonites, aluminosilicate clays (for example, bentonite), binary ternary, quaternary and higher order oxides such as e.g., $Fe_2O_3$, NiO, CaO and $CeO_2$ (binary oxides), $FeNbO_4$, $NiWO_4$ and $Sr_2TiO_4$ (ternary oxides) and $Ca_2MgSi_2O_7$ (quaternary oxide), carbides, nitrides, phosphates, and sulfides. These materials are used as supports for the gels.

Higher order oxides are oxides beyond quaternary that contain more than four elements, including oxygen. Some examples of higher order oxides include ganomalite $(Pb_9Ca_5MnSi_9O_{33})$, a lead calcium magnesium silicate, sodium calcium nickel arsenate $(NaCa_2Ni_2As_3O_{12})$ and barium copper europium lanthanum thorium oxide $(Ba_{1.33}La_{0.67}Eu_{1.5}Th_{0.5}Cu_3O_{8.89})$.

Catalytically active elements, which can be present as oxides, reduced metals, and in some cases phosphates of Group 1 (Li, Na, K, Rb, Cs), Group 2 (Be, Mg, Ca, Sr and Ba), Group 3 (Y, La) and the lanthanides (Ce, Pr, Nd, Sm, Eu, Gd, Tb, Dy, Ho, Er, Tm Yb and Lu) of the Periodic Table can be used in C—H activation catalytic chemistries. Examples include methane coupling reactions to produce ethane and ethylene. In combination with other oxides of Groups 5, 6, 7, 8, 9, 10 of the Periodic Table, Groups 1, 2, 3 and the lanthanides can also be used for other oxidation chemistries. Alkane and olefin oxidation are two examples. Group 5 (V, Nb, Ta), Group 6 (Cr, Mo, W), Group 7 (Mn, and Re), and Group 9 (Fe, Ru, Os), can be used for oxidation reactions of alkanes and olefins. Two examples are the oxidation of butane to maleic anhydride and propylene oxidation to form acrolein. Elements of Group 10 (Ni, Pd, Pt) and Group (11, Cu. Ag, and Au) can be used for alkane and olefin oxidation reactions, CO abatement, and for Pd, Pt, hydrogenation chemistries such as hydrogenation of ethylene to ethane. Ag and its oxides can be used in epoxidation reactions, such as the epoxidation of ethylene to produce ethylene oxide. Elements of Group 15, especially P, As, Sb Bi can be used for oxidation reaction chemistries, such as the ammoxidation of propylene to acrylonitrile, especially when combined with elements of Group 6 (Cr, Mo, and W) to form various oxide combinations. Elements and their oxides of Group 16 (S, Se and Te) can be used for dehydrosulfurization chemistries, which are used to treat sulfur containing streams from petroleum distillates.

The gel is prepared from at least one soluble compound comprising an inorganic element precursor wherein at least one element is selected from the group consisting of Group 1 (i.e., Li, Na, K, Rb and Cs); Group 2 (i.e., Be, Mg, Ca, Sr and Ba); Group 3 (i.e., Y and La); Group 4 (i.e., Ti, Zr and Hf); Group 5 (i.e., V, Nb and Ta); Group 6 (i.e., Cr, Mo and W); Group 7, (i.e., Mn and Re); Group 8 (i.e., Fe, Ru and Os); Group 9 (i.e., Co, Rh and Ir); Group 10 (Ni, Pd and Pt); Group 11 (Cu, Ag and Au); Group 12 (i.e., Zn and Cd); Group 13 (i.e., B, Al and In); Group 14 (i.e.; Si, Ge, Sn and Pb); Group 15 (i.e., P, As, Sb and Bi); Group 16 (i.e., S, Se and Te) and lanthanides (i.e.; Ce, Pr, Nd, Sm, Eu, Gd, Tb, Dy, Ho, Er, Tm, Yb and Lu) of the Periodic Table.

In the present invention one or more inorganic alkoxides or salts thereof is used as starting material, or precursors, for preparing the gels. The gel-forming precursor comprises at least one soluble compound comprising an inorganic element wherein the element is selected from the group consisting of aluminum, silicon, titanium zirconium, niobium, tantalum, vanadium, molybdenum and chromium. The alkoxides are the preferred compounds, and metal alkoxides are most preferred.

The inorganic metal alkoxides used in this invention may include any alkoxide which contains from 1 to 20 carbon atoms and preferably 1 to 5 carbon atoms in the alkoxide group, which preferably are soluble in the liquid reaction medium. Examples include, but are not limited to, tantalum n-butoxide, titanium isopropoxide, aluminum isopropoxide and zirconium isopropoxide. These alkoxides are preferred.

Inorganic materials have a range of pore sizes. Pore dimensions for some inorganic materials are relatively small. The present invention discloses gel-forming precursors that fit within the pore structure of the solid materials that are used. Commercially available alkoxides can be used. However, inorganic alkoxides can be prepared by other routes.

Inorganic alkoxides can be prepared in various ways. One method of preparation includes direct reaction of zero valent metals with alcohols in the presence of a catalyst. Many alkoxides can be formed by reaction of metal halides with alcohols. Also, alkoxy derivatives can be synthesized by the reaction of the alkoxide with alcohol in a ligand interchange reaction. Direct reactions of metal dialkylamides with alcohol also form alkoxide derivatives. Additional methods for preparing alkoxides are disclosed in "Metal Alkoxides" by D. C. Bradley et al., Academic Press, (1978).

The gel formed in the composition of the present invention is made by preparing one or more non-aqueous alkoxide (or salt) solutions and a separate solution of a protic solvent, such as water. Promoters and other reagents may be added to the solution(s) of alkoxides. When the alkoxide solution is mixed with the protic solvent the alkoxide hydrolyzes and cross-links to form a gel.

The solvent media used in the process generally should be a solvent for the inorganic alkoxide or alkoxides which are utilized and the additional metal reagents and promoters which are added in synthesis. Solubility of all components in their respective media (aqueous and non-aqueous) is preferred to produce highly dispersed materials. By using soluble reagents in this manner, mixing and dispersion of the active metals and promoter reagents can be near atomic, in fact mirroring their dispersion in their respective solutions. The precursor gel thus produced by this process will contain highly dispersed active metals and promoters. High dispersion results in catalyst metal particles in the nanometer size range. These particles are substantially contained, or substantially localized, within the pores of the solid material.

Typically, the concentration of the amount of solvent used is linked to the alkoxide content. A molar ratio of 26.5:1 ethanol:total alkoxide can be used, although the molar ratio of ethanol:total alkoxide can be from about 5:1 to 53:1, or even greater. If a large excess of alcohol is used, gelation will not generally occur immediately; some solvent evaporation will be needed. At lower solvent concentrations, it is thought that a heavier gel will be formed having less pore volume and surface area.

In the process of the present invention, the alkoxide solution with other reagents, water and additional aqueous solutions are contacted in the presence of a solid having pores. Due to the surface area provided by the porous character of the solid material, hydrolysis and condensation occurs substantially within the pores of the solid to form the gel.

The amount of water utilized in the reaction is the amount calculated to hydrolyze the inorganic alkoxide in the mixture. A ratio lower than that needed to hydrolyze the alkoxide species will result in a partially hydrolyzed material which, in most cases, would reach a gel point at a much slower rate, depending on the aging procedure and the presence of atmospheric moisture. Generally, a molar ratio of water:alkoxide from about of 0.1:1 to 10:1 is used.

Reaction conditions and choice of gel-forming precursor (i.e., a precursor which can react, hydrolyze and cross-link to form the gel) favors rapid hydrolyses and condensation reactions inside the pores of the solid material. These hydrolyses and condensation reactions need to be more rapid than any reactions that occur outside the pores of the solid material.

The molar ratio of the total water added to total catalytically active element added (for example, Ti, Zr, Ta, and Al), including water present in aqueous solutions, varies according to the specific inorganic alkoxide used. For tantalum (alkoxide)$_5$ ratios close to 5:1 can be used. Also, a ratio of 4:1 can be used for zirconium(alkoxide)$_4$ and titanium (alkoxides)$_4$. The addition of acidic or basic reagents to the inorganic alkoxide medium can have an effect on the kinetics of the hydrolysis and condensation reactions, and the microstructure of the oxyhydroxide matrices derived from the alkoxide precursor that comprises the soluble inorganic element. Generally, a pH within the range of from 1 to 12 can be used, with a pH range of from 1 to 6 being preferred.

The first addition step is done under conditions of incipient wetness. The order of addition is not important, i.e., the either the protic solvent or the non-aqueous solvent can be added initially. The second addition step can optionally be done under incipient wetness conditions.

After gel formation occurs within the pores of the solid material, it may be necessary to complete the gelation process with some aging of the gel composition. This aging can range form one minute to several days. In general, the gel is aged in the pores of the solid material at room temperature in air for at least several hours.

Removal of solvent from the gel composition can be accomplished by several methods. Removal by vacuum drying or heating in air results in the formation of a xerogel. A gel that is an aerogel of the material typically can be formed by charging in a pressurized system such as an autoclave. The gel composition can be placed in an autoclave where it can be contacted with a fluid above its critical temperature and pressure by allowing supercritical fluid to flow through the gel material until the solvent is no longer being extracted by the supercritical fluid. In performing this extraction to produce an aerogel material, various fluids can be utilized at their critical temperature and pressure. For example, fluorochlorocarbons typified by Freon® fluorochloromethanes (e.g., Freon® 11 ($CCl_3F$), 12 ($CCl_2F_2$) or 114 ($CClF_2CClF_2$), ammonia and carbon dioxide are all suitable for this process. Typically, the extraction fluids are gases at atmospheric conditions. The pores collapse due to the capillary forces at the liquid/solid interface are avoided during drying.

The gels formed within the pores of the solid material, whether they are xerogels or aerogels, can be described as precursor salts dispersed in an oxide or oxyhydroxide matrix. The theoretical maximum for hydroxyl content corresponds to the valence of central metal atom. Hence, $Ta_2(O_{2-x}(OH)_x)_5$ possesses a theoretical hydroxyl maximum when x is 2. The molar $H_2O$:alkoxide ratio can also impact the final xerogel stoichiometry; in this case, if $H_2O$:Ta is less than 5, there will be residual —OR groups in the unaged gel. However, reaction with atmospheric moisture will convert these to the corresponding —OH, and —O groups upon continued polymerization and dehydration. Aging, even under inert conditions, can also effect the condensation of the —OH, eliminating $H_2O$, through continuation of crosslinking and polymerization, i.e., gel formation.

The gel compositions of the present invention have utility as catalysts or as improved catalyst supports. The solid material having pores provides mechanical integrity for the gel and generally does not inhibit the catalytic properties of the gel. The mechanical integrity permits easier handling and transportation of the gel compositions since, without the solid material, these compositions are fluffy and powder-like, and not easily contained. In turn, the gel compositions disclosed herein reduce waste and therefore, is more cost efficient.

One particular use of the compositions of the present invention is in the dehydrogenation of $C_2$ to $C_{10}$ hydrocarbons. In the dehydrogenation process disclosed herein, the hydrocarbon feed that can be used in the present invention includes any $C_2$ to $C_{10}$ hydrocarbon with ethane, propane, isobutane and isooctane (2,2,4-trimethylpentane) being preferred. The gel compositions contained within the pores of the solid materials disclosed in the present invention can be used as catalysts by contacting the gel composition with the hydrocarbon feed in a dehydrogenation process in a reactor. The contacting step may be done in various types of reactors, including a fixed bed, moving bed, fluidized bed, ebullating bed and entrained bed. The less saturated hydrocarbon reaction products of this invention can be separated by conventional means such as distillation, membrane separation and absorption.

The gas hourly space velocity (GHSV) of the feed gas generally is in the range of from about 100 to about 3000 cc hydrocarbon feed/cc gel composition/hour, preferably from about 500 to about 1000 cc hydrocarbon feed/cc gel composition/hour. The operating pressure is generally in the range of from about 7 kPa to about 700 kPa, preferably from about 7 kPa to about 400 kPa. The dehydrogenation reaction temperature generally is in the range of from about 300° C. to about 650° C., preferably from about 450° C. to 600° C.

The gel-containing compositions of this invention can be regenerated periodically to remove coke. The regeneration is done by conventional techniques of carbon removal such as heating with an oxygen-containing gas, preferably air.

The compositions of the present invention are also useful as catalyst supports. For example, a chromium/aluminum gel supported in eta-alumina, prepared as described in Example 1 below, can be impregnated with a water soluble compound of platinum. One such example would be impregnation with $H_2PtCl_4$. The impregnated support is then dried and heated to 400° C. in a 5% hydrogen/nitrogen stream for 4 hours and then cooled. The reduced supported catalyst is then suspended in a solvent containing 1-hexene. The suspension is then heated at about 100° C. with stirring under a hydrogen atmosphere at about 3000 kPa for about two hours. Hexane can be separated from the reaction mixture.

In addition to the utility disclosed above, the compositions of the present invention also can be used as catalyst supports for oxidation (e.g., supported cobalt) and hydroformylation (e.g. supported rhodium) reactions.

The process for making the present invention may be implemented by using combinatorial methods for the rapid syntheses of catalysts. Such methods would permit the production of these catalysts using robotic tools, such as liquid delivery system, to a solid having pores, as described in the present invention, to create gel compositions substantially in the pores of the solid.

EXAMPLES

The catalyst charge was 2 mL for all the examples.
General Procedure for Catalyst Testing Catalyst tests were performed in a fixed bed continuous flow quartz reactor with 6.4 mm id. The catalyst charge was 2.0 mL of −12/+20 mesh (−1.68/+0.84 mm) granules. The reactor tube was heated in a tube furnace to 550° C. in flowing nitrogen until the temperature was stable. A thermocouple inside the catalyst bed was used to measure temperature. Once the desired temperature was achieved, a feed consisting of 50% isobutane/50% nitrogen (Examples 1 to 4) or a feed consisting of 50% propane/50% nitrogen (Examples 5 to 6) were passed over the catalyst bed. The contact times 3.2 seconds in all the examples. The entire product stream was analyzed on-line using sampling valves and an HP 5890 chromatogram (TCD)/HP 5971 mass selective detector.

The gel compositions prepared in the Examples below were used in dehydrogenation processes. The results are tabulated and are shown below in Table 1 (isobutane dehydrogenation) and Table 2 (propane dehydrogenation).

| Legend |
|---|
| $C_3$ is $CH_3CH_2CH_3$ |
| iC4 is $(CH_3)_2CHCH_3$ |
| Conv. is conversion |
| Sel. is selectivity |
| $C_3=$ is $CH_2=CHCH_3$ |
| iC4= is $(CH_3)_2C=CH_2$ |

Example 1

$(Cr_{0.2}Al_{0.8})_{0.0383}(eta\text{-}Al_2O_3)_{0.96169}$

A sol gel of chromium hydroxide acetate/aluminum isopropoxide contained in the pores of eta alumina was prepared as follows: eta alumina (8.0 g, $N_2$ BET surface area=401.9 $m^2$/g, pore volume=0.327474 cc/g) was used. An aqueous solution containing 0.1 M (with respect to chromium) $(Cr_3(OH)_2)(ac)_7$ was prepared by dissolving the chromium salt (4.022 g) in a sufficient quantity of commercially available ammonium hydroxide solution (28–30% $NH_4OH$ in water) to bring the solution volume to 200 mL. In a first sol gel preparation, the chromium solution (5 mL) was first added dropwise to the eta alumina support with agitation. Following addition of the aqueous solution, 0.05 M aluminum isopropoxide in isopropanol (20 mL) was slowly added to the wet support. Excess solvent was used in this preparation (however, the aluminum isopropoxide will deposit inside of the pores of the supports to graft onto it). The solid was allowed to dry in air prior to the second impregnation.

In a second cycle, additional chromium solution (2.5 mL) was added, and additional aluminum isopropoxide solution (20 mL) was added into the support. In a third cycle, 2.7 mL of the chromium solution was used, and 20 mL of the aluminum isopropoxide solution was employed. In a fourth cycle, 2.2 mL of the chromium solution was added along with 0.3 mL of NH$_4$OH solution was added, followed by 20 mL of the aluminum isopropoxide solution. The final cycle involved the addition of 2.5 mL of ammonium hydroxide solution (only) followed by 20 mL of the aluminum isopropoxide. The final material was dried under vacuum for 5 hours at 120° C. The material was pelletized and granulated and sieved on −10, +20 mesh (−2.0, +0.84 mm) screens prior to reactor evaluations. High resolution transmission electron microscopy depicted Example 1 and showed that the chromium-alumina gel is essentially within the pores of the eta-alumina solid material (support).

Example 2

$Cr_{0.0182}Al_{0.0285}(TiO_2)_{0.9533}$

A portion (7.7 mL) of the 0.1 M (with respect to chromium)solution of chromium hydroxide acetate described in Example 1 was added to titanium oxide (8 g), followed by 20 mL of the 0.05 M aluminum isopropoxide solution (described in Example 1) to add the alkoxide into the support. In a second cycle, 6.7 mL and 20 mL of the chromium and aluminum solutions, respectively, were used. In a third cycle, 4.75 mL and 20 mL of the chromium and aluminum solutions, respectively, were used. The final material was dried under vacuum for 5 hours at 120° C. The material was pelletized and granulated and sieved on −10, +20 mesh (−2.0, +0.84 mm) screens prior to reactor evaluations.

Example 3

5.261 wt % ($CrO_{1.5}$), 1.193 wt % ($AlO_{1.5}$), 93.546 wt % Bentonite Clay

Bentonite clay (8 g) was used as a support. A 2.5 mL portion of the 0.1 M (with respect to chromium) chromium hydroxide acetate solution from Example 1 was used, followed by 20 mL of the aluminum isopropoxide solution from Example 1. One additional cycle was used to bring the catalyst to the final loading. The final material was dried under vacuum for 5 hours at 120° C. The material was pelletized and granulated and sieved on −10, +20 mesh (−2.0, +0.84 mm) screens prior to reactor evaluations.

Example 4

$Cr_{0.003432}Al_{0.0137266}/C_{0.9828414}$

A 5 mL portion of the 0.1 M (with respect to chromium) chromium hydroxide acetate solution from Example 1 was added to carbon black (6.88 g) followed by 40 mL of the aluminum isopropoxide solution. In a second cycle, 5 mL of the chromium solution and 40 mL of the aluminum hydroxide solution were used. A third cycle used 5 and 40 mL, and a fourth cycle 4 and 40 mL were used. The final material was dried under vacuum for 5 hours at 120° C. The material was pelletized and granulated and sieved on −10, +20 mesh (−2.0, +0.84 mm) screens prior to reactor evaluations.

Example 5

$CrO_{0.0182}Al_{0.0285}(TiO_2)_{0.9533}$

This example was prepared as described in Example 2.

Example 6

5.261 wt % ($CrO_{1.5}$), 1.193 wt % ($AlO_{1.5}$), 93.546 wt % Bentonite Clay

This example was prepared as described in Example 3.

Example 7

$Cr_{0.003432}Al_{0.0137266}/C_{0.9828414}$ 10 grams of a sample from Example 4 was suspended in 10 mL of water containing 1 gm of $K_2PtCl_4$. The sample was heated to 400° C. in a 5% hydrogen/nitrogen stream for 4 hours and cooled. The reduced catalyst (0.100 g) was suspended in 1 mL of hexane containing 0.200 gm of 1-hexene and heated to 100° C. with 500 psig $H_2$ for 2 hours. GC analysis of the product showed greater than 95% selectivity for hexane.

TABLE 1

| | ISOBUTANE DEHYDROGENATION | | | | |
|---|---|---|---|---|---|
| Ex. No. | % iC$_4$ Conv. | % iC$_4$= Sel. | % CH$_4$ Sel. | % C$_2$-C$_4$ Sel. | % Others Sel. |
| 1 | 37.2 | 27.4 | 31.4 | 38.4 | 2.3 |
| 2 | 32.1 | 60.9 | 24.4 | 14.8 | 0 |
| 3 | 6.9 | 64.4 | 0 | 35.6 | 0 |
| 4 | 12.4 | 83.4 | 0 | 16.6 | |

TABLE 2

| | PROPANE DEHYDROGENATION | | | |
|---|---|---|---|---|
| Ex. No. | % C$_3$ Conv. | % C$_3$= Sel. | % C$_2$ Sel. | % Others Sel. |
| 5 | 23.0 | 86.4 | 8.2 | 5.5 |
| 6 | 3.2 | 55.8 | 40.0 | 4.2 |

What is claimed is:

1. A composition of matter comprising (a) a solid material having pores, and (b) a gel;
    wherein the gel is substantially localized within the pores of the solid material; and
    wherein the gel comprises at least one catalytically active element, and optionally comprises chromium when the catalytically active element is other than chromium.

2. The composition of claim 1 wherein the solid material having pores is selected from the group consisting of alumina, silica, titania, zirconia, carbon, molecular sieves, porous minerals, microporous, mesoporous and macroporous materials, montmorillonites, aluminosilicate clays, and binary, ternary, quaternary and higher order oxides, carbides, nitrides, phosphates, and sulfides.

3. The composition of claim 2 wherein said catalytically active metal is selected from the group consisting of platinum and gold.

4. The composition of claim 1 wherein said catalytically active element is chromium and said solid material having pores is alumina.

5. A gel composition comprising a gel that is substantially localized within the pores of a solid material selected from the group consisting of alumina, silica, titania, zirconia, carbon, molecular sieves, porous minerals, montmorillonite clay, alumninosilicate clays, carbides, nitrides, phosphates, and sulfides.

6. A process for preparing a composition of matter comprising (a) a solid material having pores, and (b) a gel;
    wherein the gel is substantially contained within the pores of the solid material;
    wherein the gel comprises at least one catalytically active element, and optionally comprises chromium when the catalytically active element is other than chromium;

wherein the process comprises contacting a solid material having pores with, in any order, a protic solution and a non-aqueous solution;

wherein the solution added first is at incipient wetness;

wherein one of either the protic solution or the non-aqueous solution comprises at least one soluble compound comprising an inorganic element selected from the group consisting of Li, Na, K, Rb, Cs, Be, Mg, Ca, Sr, Ba, Y, La, Ti, Zr Hf, V, Nb, Ta, Cr, Mo, W, Mn, Re, Fe, Ru, Os, Co, Rh Ir, Ni, Pd Pt, Cu, Ag, Au, Zn, Cd, B, Al, In, Si, Ge, Sn, Pb, P, As, Sb, Bi, S, Se Te, Ce, Pr, Nd, Sm, Eu, Gd, Tb, Dy, Ho, Er, Tm, Yb and Lu and lanthanides of the Periodic Table;

wherein the non-aqueous solution comprises a gel-forming precursor; and wherein gel formation occurs substantially within the pores of the solid material.

7. The process of claim 6 wherein the solid material laving pores is a catalyst support selected from the group consisting of alumina, silica, titania, zirconia, carbon, molecular sieve, porous mineral, montmorillonite clay, aluminosilicate clay, carbide, nitride, phosphate, and sulfide; and said gel-forming precursor comprises at least one soluble compound comprising an inorganic element selected from the group consisting of aluminum, silicon, titanium, zirconium, niobium, tantalum, vanadium, molybdenum and chromium.

8. The process of claim 7 wherein the catalyst support is alumina, and the gel-forming precursor is a chromium salt.

* * * * *